United States Patent
Wallenås et al.

(10) Patent No.: US 10,709,831 B2
(45) Date of Patent: Jul. 14, 2020

(54) METHOD AND APPARATUS FOR PERFORMING PERITONEAL ULTRAFILTRATION

(71) Applicant: TRIOMED AB, Lund (SE)

(72) Inventors: Anders Wallenås, Lomma (SE); Lars Wramner, Göteborg (SE); Stefan Landholm, Malmö (SE)

(73) Assignee: TRIOMED AB, Lund (SE)

( * ) Notice: Subject to any disclaimer, the term of this patent is extended or adjusted under 35 U.S.C. 154(b) by 287 days.

(21) Appl. No.: 15/122,103

(22) PCT Filed: Feb. 27, 2015

(86) PCT No.: PCT/SE2015/000011
§ 371 (c)(1),
(2) Date: Aug. 26, 2016

(87) PCT Pub. No.: WO2015/130205
PCT Pub. Date: Sep. 3, 2015

(65) Prior Publication Data
US 2017/0072125 A1 Mar. 16, 2017

(30) Foreign Application Priority Data
Feb. 28, 2014 (SE) .................................... 1430027

(51) Int. Cl.
*A61M 1/28* (2006.01)
*A61M 1/34* (2006.01)
*A61M 1/16* (2006.01)

(52) U.S. Cl.
CPC .............. *A61M 1/287* (2013.01); *A61M 1/28* (2013.01); *A61M 1/281* (2014.02); *A61M 1/282* (2014.02);
(Continued)

(58) Field of Classification Search
CPC .............. A61M 1/1656; A61M 1/1676; A61M 1/1678; A61M 1/1694; A61M 1/1696;
(Continued)

(56) References Cited

U.S. PATENT DOCUMENTS 5,980,481 A * 11/1999 Gorsuch ............. A61M 1/1678
604/28
6,228,047 B1 * 5/2001 Dadson ............... A61M 1/1656
604/29

(Continued)

*Primary Examiner* — William R Carpenter
*Assistant Examiner* — Larry R. Wilson
(74) *Attorney, Agent, or Firm* — Birch, Stewart, Kolasch & Birch, LLP

(57) ABSTRACT

Method and apparatus for ultrafiltration of a patient being overhydrated due to congestive heart failure, comprising a cassette having four inlets/outlets. A patient tube is connected to a patient connector, intended to be connected to a patient line for access to a peritoneal cavity of the patient. The patient tube comprises a flow pump for addition and removal of a peritoneal fluid between the cassette and the peritoneal cavity. The fluid is introduced into an intermittent bag controlled by an intermittent valve and then returned the same way back to the peritoneal cavity. Glucose is metered into the fluid entering the peritoneal cavity by means of a glucose pump. Glucose is replenished continuously or intermittently for keeping a concentration of the osmotic agent substantially constant in the peritoneal cavity. After treatment, the peritoneal fluid is drained to a drain bag, wherein the drain tube comprises a drain valve and an albumin filter.

23 Claims, 3 Drawing Sheets

(52) U.S. Cl.
CPC ............ *A61M 1/285* (2013.01); *A61M 1/288* (2014.02); *A61M 1/34* (2013.01); *A61M 1/1609* (2014.02); *A61M 2205/12* (2013.01); *A61M 2205/3334* (2013.01); *A61M 2205/3344* (2013.01); *A61M 2205/75* (2013.01)

(58) Field of Classification Search
CPC ........ A61M 1/28; A61M 1/281; A61M 1/282; A61M 1/285; A61M 1/287; A61M 1/288; A61M 1/34; A61M 1/3413; A61M 2205/12; A61M 2205/3331; A61M 2205/3334; B01D 61/24; B01D 61/243; B01D 61/246; B01D 61/30; B01D 2321/04; B01D 2321/2083; B01D 2321/12
USPC ........................................ 210/636, 645, 646
See application file for complete search history.

(56) References Cited

U.S. PATENT DOCUMENTS

| | | | | |
|---|---|---|---|---|
| 6,284,140 | B1 * | 9/2001 | Sommermeyer | A61K 31/715 210/646 |
| 6,585,682 | B1 * | 7/2003 | Haraldsson | A61M 1/1696 604/28 |
| 8,708,950 | B2 * | 4/2014 | Scarpaci | A61M 1/28 604/28 |
| 2007/0179431 | A1 * | 8/2007 | Roberts | A61M 1/1696 604/29 |
| 2012/0029325 | A1 * | 2/2012 | Neftel | A61M 1/282 600/309 |

* cited by examiner

METHOD AND APPARATUS FOR PERFORMING PERITONEAL ULTRAFILTRATION

FIELD OF INVENTION

The present invention relates to an apparatus and method for performing peritoneal ultrafiltration of a patient, for example due to congestive heart failure.

BACKGROUND

Diuretic-resistant congestive heart failure is a problem of growing significance. It is related closely to the cardio-renal syndrome, which is characterized by chronic abnormalities in cardiac function, causing impaired renal function and progressive chronic kidney disease.

Congestive Heart Failure patients can benefit from fluid removal by ultrafiltration. These patients normally have functional kidneys, but suffer from fluid overload. The kidneys of these patients are generally healthy but are not fully functioning due to the failing heart with increased venous blood pressure and sometimes low arterial blood pressure. Because the kidneys are not fully functioning, fluids build up in the patient and the fluid overload contributes to stress on the already failing heart. In addition, secretion of certain electrolytes, such as sodium ions and potassium ions, may be impaired.

The proper control of sodium and water balance is of vital importance because up to 80% of hospitalizations from Congestive Heart Failure are due to acute overhydration and only 5% are due to low cardiac output.

The patent document U.S. Pat. No. 7,135,008B2 discloses a method and apparatus for the extracorporeal treatment of blood by utilizing a peripherally inserted dual lumen catheter assembly for the continuous removal and return of blood for renal replacement treatment, in particularly, treatment of congestive heart failure and fluid overload by ultrafiltration. A catheter is inserted in a peripheral vein and maneuvered upward through the vascular system to access the reservoir of blood in the large or great veins for continuous blood withdrawal and treatment. Air-tight connectors are incorporated in the catheter assembly to overcome the untoward effects of negative pressure in blood withdrawal.

However, ultrafiltration via extracorporeal treatment of blood, results in risks associated with access to the vascular system. In addition, the ultrafiltration may be excessive resulting in hypotension.

A promising ultrafiltration method which do not use extracorporeal blood treatment is peritoneal dialysis, in which the endogenous peritoneal membrane is used for ultrafiltration. A peritoneal ultrafiltration fluid is installed in the peritoneal cavity. The fluid comprises an osmotic agent, such as glucose or Icodextrin or others, causing ultrafiltration. Peritoneal ultrafiltration is more gentle to the patient and seldom results in hypotension. In addition, the peritoneal ultrafiltration may be used daily outside the hospital without the need for medically trained professionals.

With the present PD regiments, glucose based fluids must be replaced every four hours and has optimal ultrafiltration for only 2 to 3 hours. Each replacement takes about one hour and increases the risk of infection. This reduces the freedom and quality of life for the patients. Automated PD dialysis machines are know in the prior art, but they are cumbersome and are not optimized for merely ultrafiltration, but concentrate on urea nitrogen removal.

However, the use of glucose may result in the absorption of glucose into the circulation, which may lead to hyperglycemia, hyperinsulinemia, and obesity. Icodextrin may cause other problems.

It is also known that peritoneal dialysis often results in removal of albumin and other important constituents of the blood and body.

Thus, there is a need for a peritoneal dialysis fluid comprising glucose, which is optimized with regard to peritoneal ultrafiltration of patients with heart failure. In addition, there is a need for a method and an apparatus for performing peritoneal ultrafiltration.

SUMMARY OF THE INVENTION

Accordingly, an object of the present invention is to mitigate, alleviate or eliminate one or more of the above-identified deficiencies and disadvantages singly or in any combination.

In an aspect, there is provided an apparatus for ultrafiltration of a patient, for example a patient being overhydrated due to congestive heart failure, comprising: a cassette having four inlets/outlets; a patient tube for connection of a patient connector, intended to be connected to a patient line for access to a peritoneal cavity of the patient, to a first inlet of the cassette, wherein the patient tube comprises a flow pump for addition and removal of a peritoneal fluid between the cassette and the peritoneal cavity; an intermittent tube for connection of an intermittent bag to a second inlet of the cassette, wherein the intermittent tube comprises an intermittent valve; a drain tube for connection of a drain bag to a third inlet of the cassette, wherein the drain tube comprises a drain valve; and a glucose tube for connection of a glucose bag comprising glucose at a high concentration to a fourth inlet of the cassette, wherein the glucose tube comprises an glucose pump for addition of glucose to the cassette; whereby glucose is replenished for keeping a concentration of the osmotic agent substantially constant in the peritoneal cavity.

According to an embodiment, the first and second inlets of the cassette are arranged at one side of the cassette and the third and fourth inlets of the cassette are arranged at the other side of the cassette. The intermittent bag may be smaller than 500 ml, 400 ml, 300 ml, 200 ml, such as 160 ml. A glucose meter may be arranged for measuring glucose concentration of peritoneal fluid entering or leaving the cassette. The glucose meter may be arranged in said drain tube downstream of said drain valve, whereby glucose concentration is measured only when the drain valve is open. A pressure meter may be arranged for measuring pressure of peritoneal fluid adjacent the patient connector. Another pressure meter may be arranged for measuring pressure inside said cassette. Moreover, a flow meter may be arranged in the patient tube.

In another embodiment, the intermittent bag is replace by a second patient connector, intended to be connected to a second patient line for access to the peritoneal cavity of the patient.

In a further embodiment, the patient tube, the patient connector, the patient line, the first inlet, the cassette, the intermittent tube, the intermittent bag, the second inlet of the cassette, are all arranged without any adsorbent material or dialyzer. The drain tube may comprise an albumin filter for preventing albumin from passing to the drain bag during draining of the peritoneal cavity.

In another aspect, there is provided a method for ultrafiltration of a patient, for example a patient being overhydrated due to congestive heart failure, which patient has a predetermined volume of peritoneal fluid installed in a peritoneal cavity; comprising: removing peritoneal fluid from the peritoneal cavity, via a patient line, a patient connector, and a flow pump to a first inlet of a cassette, and further, via a second inlet, an open intermittent valve, and an intermittent tube to an intermittent bag; subsequent return of peritoneal fluid from said intermittent bag the same way in the opposite direction; wherein concentrated glucose solution is, during said return of peritoneal fluid, simultaneously entered to the cassette via a fourth inlet by means of a glucose pump from a glucose concentration fluid bag for being diluted in the flow of peritoneal fluid and entered into the peritoneal cavity; whereby glucose is replenished to the peritoneal fluid in the peritoneal cavity.

In an embodiment, the removal flow and return flow may pass through tubes and spaces free from adsorbent materials and/or free from dialyzers.

In another embodiment, the peritoneal cavity is drained from peritoneal fluid after finalized peritoneal ultrafiltration, by removing peritoneal fluid from the peritoneal cavity to a drain bag by means of said flow pump, through an albumin filter, until the peritoneal cavity is empty, whereupon the flow pump is reversed and returns a small amount of peritoneal fluid from the drain bag via the albumin filter to the peritoneal cavity in order to return albumin gathered by the albumin filter. The draining of the peritoneal fluid may take place via the patient line, the patient connector, and the flow pump to the first inlet of the cassette, and further, via a third inlet, an open drain valve and the albumin filter to the drain bag.

In a further embodiment, the removal flow and the return flow each time may comprise a maximum volume of less than 500 ml, 400 ml, 300 ml, 200 ml, such as 160 ml.

In a still further embodiment, a peritoneal fluid comprising less than 0.5%, such as less than 0.2%, for example 0.1% or 0% glucose is initially introduces into the peritoneal cavity before the start of the removing and returning of the peritoneal fluid, whereupon the glucose concentration is increased to a predetermined treatment concentration during a predetermined time, such as during between 30 minutes and 60 minutes.

In a further aspect, there is provided a method for ultrafiltration of a patient, for example a patient being overhydrated due to congestive heart failure, which patient has a predetermined volume of peritoneal fluid installed in a peritoneal cavity, comprising: removing peritoneal fluid from the peritoneal cavity, via a first patient line, a patient connector, and a flow pump to a first inlet of a cassette, and further, via a second inlet/outlet of the cassette, an open intermittent valve, and an intermittent tube to a second patient line; wherein concentrated glucose solution is, during said flow of peritoneal fluid, simultaneously metered to the cassette via a fourth inlet by means of a glucose pump from a glucose concentration fluid bag for being diluted in the flow of peritoneal fluid and entered into the peritoneal cavity; whereby glucose is replenished to the peritoneal fluid in the peritoneal cavity.

In a still further aspect, there is provided a use of a peritoneal fluid for treatment of overhydration due to congestive heart failure by peritoneal ultrafiltration, wherein peritoneal fluid is removed from the peritoneal cavity of the patient and returned to the peritoneal cavity replenished with glucose, for maintaining a substantially constant concentration of glucose in the peritoneal fluid.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

Figure 1:
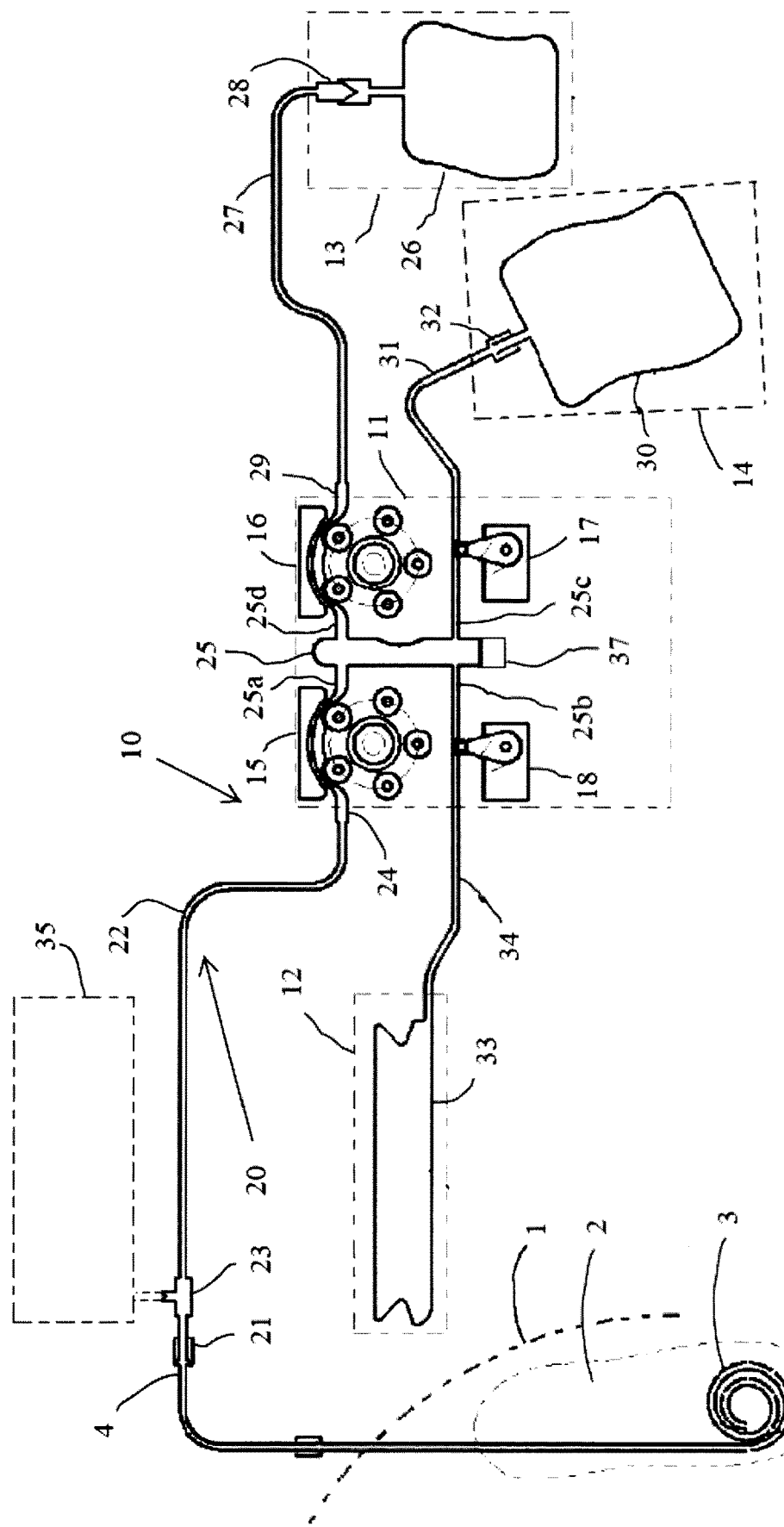
FIG. 1 is a schematic diagram of a first embodiment of an apparatus for providing an ultrafiltration fluid to a patient.

FIG. 1 discloses a patient 1, which is provided with a patient line 3, which may be a conventional peritoneal catheter. The patient line 3 connects the patient's peritoneal cavity 2 with the surrounding environment. The patient line 3 ends with a connector 4 of standard type, for example a Luer connector. The provision of the patient line is a standard procedure and is made at a hospital. After a few days, the patient line may be used for entering and removing a peritoneal fluid into the peritoneal cavity. The peritoneal fluid contacts a peritoneal membrane comprising capillary blood vessels. The peritoneal fluid will exchange ions and substances with the blood. Peritoneal dialysis has been performed routinely for several decades and was used already during the 1940's.

An apparatus 10 according to a first embodiment of the invention is shown in FIG. 1 and comprises a tube set 20, having a cassette 25 comprising four inlets from: a flow pump 15, a glucose pump 16, a drain valve 17 and an intermittent valve 18.

The pumps 15 and 16 are shown as peristaltic pumps of a type commonly used in a dialysis apparatus. However, other types of pumps may be used.

The valves are electrically operated pinch valves which act upon a tube for occlusion of the tube. However, any type of valve may be used, including manually operated clamps.

The tube set comprises a connector 21, which mates with the connector 4 of the patient line 3. The connector 21 is arranged at a distal end of a patient tube 22. The patient tube 22 comprises a port 23 adjacent the end connector 21.

A proximal end of the patient tube 22 is connected to a pump segment 24 passing through the flow pump 15. The other end of the pump segment 24 is connected to a first inlet 25a of the cassette 25. Thus, the cassette 25 is connected to the end connector 21.

The tube set further comprises a glucose bag 26, which is connected to the cassette 25 via a glucose tube 27. The glucose tube 27 is connected to a pump segment 29 passing through the glucose pump 16 and further to a fourth inlet 25d of the cassette 25. A connector or spike 28 is arranged at the end of the glucose tube 27 for being inserted in the glucose bag 26 for establishing fluid communication between the glucose bag 26 and the glucose tube 27. Thus, the glucose bag 26 is connected to the cassette 25. Alternatively, the glucose bag is permanently attached to the glucose tube 27 or connected to the glucose tube by a Luer connector or other similar connector.

The tube set further comprises a drain bag 30, which is connected to a drain tube 31 via a connector 32. The drain tube 31 is connected to a third inlet 25c of the cassette 25. The drain valve 17 acts upon the drain tube 31 for occluding the drain tube when activated. Thus, the drain bag 30 is connected to the cassette 25.

The tube set further comprises an intermittent bag 33 connected to an intermittent tube 34. The intermittent tube 34 is connected to a second inlet 25b of the cassette 25. The intermittent pinch valve 18 acts upon the intermittent tube 34 for occluding the intermittent tube when activated. Thus, the intermittent bag 33 is connected to the cassette 25.

The tube set may be PVC tubes of a medical grade. The pump segments may be made by silicon tubes. The peristaltic pump may also operate as a flow meter, since a specific volume of fluid is normally pumped per revolution of the pump.

It is noted that first 25a and second 25b inlets of the cassette 25 are arranged at the on (left) side of the cassette 25. These inlets are associated with the handling of the peritoneal fluid which is passed between the peritoneal cavity and the intermittent bag 33.

On the other hand, the third 25c and fourth 25d inlets are arranged at the other (right) side of the cassette 25. These inlets are arranged for being connected to external bags, namely the glucose bag 26 and the drain bag 30. This arrangement results in a more safe operation of the device in that the different connections will not easily be mixed up. Since the patient tube 22 extends to the left and the other tubes 27, 31 to the right, it is easy to make the right connection of the patient tube 22 to the patient line 3 and not intermix it with the other connectors 28 and 32.

The apparatus 10 and tube set 20 may be arranged in four enclosures as indicated by broken lines in FIG. 1. Thus, the two pumps 15, 16 and the two pinch valves 17, 18 may be arranged in one enclosure as indicated by broken lines 11, which additionally may comprise necessary electronic circuits for operating the apparatus, including any batteries, processor board and graphical interface including operating buttons. The intermittent bag 30 may be arranged in a separate enclosure 12 and the glucose bag 26 may be arranged in a separate enclosure 13 and the drain bag may be arranged in a separate enclosure 14. All the enclosures 11, 12, 13, 14 may be arranged in a wearing equipment intended to be worn by the patient.

Alternatively, the apparatus 10 is assembled inside a bag or supporting structure, and the tube set 20 is arranged at the apparatus during initiation thereof.

The apparatus 10 according to the first embodiment may be operated in the following manner.

The apparatus 10 is set-up by arranging the wearing equipment on a patient. First, the tube set should be primed by passing a sterile fluid along the fluid lines. Such priming ensures that possible toxic products at the inner side of the tubes are removed. In addition, any bacteria may be removed, for example originating from an aseptic handling of the tube set. Moreover, any air inside the tube set is removed. Finally, a possible leak of the tube set will be discovered, so that another set can be used.

One example of a priming sequence is the following: A priming bag 35 shown by broken lines in FIG. 1 and comprising sterile isotonic priming solution (for example about 2 liters of sterile 0.9% saline solution) is connected to the port 23 at the distal end of the patient tube 22. The end connector 21 is closed by a lid (not shown). When a priming button is pressed, the priming procedure starts.

The priming procedure starts with opening of the drain valve 17, whereupon the flow pump 15 is started and operated in a forward (clockwise) direction. Fluid from the priming bag passes via port 23 to patient tube 22 and further to the pump segment 24 and to the cassette 25. From the cassette 25, the only open connection is via drain valve 17 to the drain bag 30.

After some time, the drain valve 17 is closed and the intermittent valve 18 is opened, whereupon the priming fluid is pumped into the intermittent bag 33, until it is (almost) full. Then, the flow pump 15 is operated in its reverse (counterclockwise) direction for removing the priming fluid from the intermittent bag and back to the priming bag, until the intermittent bag is empty. Possible air inside the intermittent bag is removed in this step. Then, the intermittent valve 18 is closed and the drain valve 17 is opened and the flow pump 15 is again operated in the forward direction, for pumping the rest of the priming fluid to the drain bag 30. During or before priming of the patient tube 22, a glucose bag 26 is connected to the spike 28, whereupon the glucose pump 16 is started. A small amount of glucose solution is pumped from the glucose bag 26 via the glucose tube 27 to the cassette 25 for rinsing the glucose tube.

When the priming is completed and the priming bag 35 is empty, it may be removed from the port 23, which is closed. Before the priming bag is empty, the lid at the end of connector 21 may be removed for a short time duration, whereby sterile fluid rinse the connector 21, whereupon the lid is added again.

The drain bag 30, which is filled with priming fluid, is removed and a new bag comprising peritoneal fluid to be used for peritoneal ultrafiltration is connected to connector 32. The patient is connected to the patient tube 22 by removing the lid from the patient connector 21 and attaching the connector to the patient line connector 4. The drain valve 17 is opened and the flow pump 15 is operated in its reverse direction for entering the peritoneal fluid from bag 30 into the peritoneal cavity of the patient.

When the treatment is ended (after several hours), surplus fluid is finally removed from the patient to the drain bag.

Other priming procedures may be used. For example, the priming fluid collected in drain bag 30 may be pumped back to the priming bag 35 in a last step, whereupon the priming bag 35 is discarded with its contents.

Another method may be to pump the priming fluid from priming bag 35 to the intermittent bag (a priming fluid volume of 200 ml would be sufficient) by opening the intermittent valve 18 and operating the pump 15 in the forward direction, until the intermittent bag is filled. Then, the pump 15 is reversed and the fluid from the intermittent bag 33 is returned together with a small amount of fluid from the glucose bag 26 until the intermittent bag 33 is empty, whereby possible air in the intermittent bag and cassette is removed. Finally, a small amount of a peritoneal fluid in the drain bag 30 is pumped to the priming bag by opening drain valve 17 and closing intermittent valve 18. Now all lines have been primed as desired and the priming bag 35 can be removed and peritoneal fluid in the drain bag 30 can be installed in the patient.

Alternatively, a conventional CAPD-bag-set may be connected to the port 23 or connector 4 for the initial installation of initial peritoneal fluid and peritoneal fluid may be entered into the peritoneal cavity by gravity feed. In this case, the drain bag 30 is initially empty. In the same way, the final emptying of the peritoneal cavity after a full treatment may take place by connection of a separate drain bag to the port 23 and draining the peritoneal cavity by gravity by placing the drain bag in a low position.

If the peritoneal fluid in bag 30 comprises glucose of a desired concentration (such as 1.5%), the glucose pump 16 is not activated during the initial introduction of peritoneal fluid to the peritoneal cavity. However, in another embodiment, the peritoneal fluid in bag 30 comprises all components of a peritoneal solution except glucose, and glucose is added during the initial installation in a desired proportion by activating the glucose pump 16. Alternatively, the glucose concentration of the peritoneal fluid is slowly increased during the first cycles, for example during 30 to 60 minutes, to a predetermined glucose concentration. The initial glucose concentration of the initially installed peritoneal fluid may be less than 0.5%. The glucose concentration may be 0.1%, corresponding to normal physiological glucose concentration, or 0% as indicated above.

The standard components of a peritoneal solution in addition to glucose are: sodium chloride, sodium lactate, calcium chloride and magnesium chloride. In addition, potassium chloride may be included. Lactate may be replaced by acetate or bicarbonate.

When the peritoneal fluid comprising glucose has been installed in the peritoneal cavity, exchange of substances takes place between the installed fluid and the blood. In particular, glucose is slowly absorbed by the blood, since the concentration of glucose in the peritoneal fluid is larger than the glucose concentration in blood. However, since the absorption of glucose is slow, water will diffuse in the other direction through the walls of the capillaries into the peritoneal cavity, due to osmotic pressure of the glucose solution, in order to dilute the peritoneal fluid. As long as the concentration of glucose in the peritoneal fluid is larger than in blood, such water transport takes place. Such water transport is equivalent to ultrafiltration. Since the blood will lose some water, this water loss will be replaced in the blood from other portions of the body, resulting in removal of surplus water from the tissue. However, a too fast removal of water from the blood should be avoided, since the blood may become too concentrated and viscous.

The glucose, which has been absorbed into the blood, is taken care of by the body system, in particular the insulin system, which keeps the glucose concentration in blood within safe limits, normally between 4 to 7 mmol/liter, corresponding to 0.72 to 1.26 g/l.

The glucose absorbed by the blood from the peritoneal cavity needs to be replaced in the peritoneal cavity in order to maintain the glucose gradient and ultrafiltration. The principle used in the embodiments is that a more or less continuous replacement of glucose is performed in order to achieve a substantially constant ultrafiltration, which is believed to alleviate symptoms.

This is accomplished in the following manner. After a short time of for example twenty minutes, the intermittent valve 18 is opened and the flow pump 15 is operated in the forward direction, whereby fluid is removed and pumped from the peritoneal cavity via the cassette 25 to the intermittent bag, which may have a volume of about 160 ml. The flow rate may be about 16 ml/min. When a predetermined amount of fluid has been entered into the intermittent bag, for example 100 ml (or a maximum of 160 ml), the flow pump 15 is operated in the reverse direction for returning the fluid in the intermittent bag 33 to the patient. The glucose pump 16 continuously adds glucose to the returned peritoneal fluid in the cassette 25. The addition of glucose takes place at a rate calculated to replaces the glucose, which has been absorbed by the blood. The procedure is repeated intermittently after another twenty minutes etc.

Thus, the peritoneal fluid in the peritoneal cavity is replenished with fresh glucose intermittently. However, the replenishment cycle takes place relatively often, so that the glucose concentration in the peritoneal fluid inside the peritoneal cavity is substantially constant. Thus, a substantially constant ultrafiltration takes place.

The intermittent bag 33 is designed to be smaller than the amount of fluid installed in the peritoneal cavity. This makes it impossible to remove all peritoneal fluid in the peritoneal cavity. The intermittent bag 33 should be smaller than 500 ml, such as smaller than 400 ml, 300 ml or even smaller than 200 ml. In the present embodiment, the intermittent bag is 160 ml. If all peritoneal fluid inside the peritoneal cavity is removed, the ultrafiltration stops. Since the time for removal and installation of peritoneal fluid is relatively long and should be gentle, such ultrafiltration stops would be undesirable. Thus, only a small portion of the peritoneal fluid in the peritoneal cavity is removed during each step or cycle. The amount removed need not be the complete volume of the intermittent bag, but may be smaller, such as 100 ml in a bag of 160 ml as mentioned above.

The flow pump may be operated at a speed of 20 ml/min. Thus, the removal of 100 ml of fluid from the peritoneal cavity and return of the same amount (replenished by glucose) may take about 10 minutes. Then, the flow pump may be kept stopped for 0 to 50 minutes, until a next replacement cycle is started. Thus, the total replacement cycle is 10 to 60 minutes.

Ultrafiltration also results in that the volume of peritoneal fluid inside the peritoneal cavity increases. Such increase of volume may result in that the pressure inside the peritoneal cavity increases, which counteracts ultrafiltration.

In order to counteract such increase of volume inside the peritoneal cavity, the following procedure may be used. At the start of a replenishment cycle, the intermittent valve 18 is kept closed and the drain valve 17 is opened and a predetermined amount of peritoneal fluid is removed and pumped into the drain bag 30, for example 50 ml per intermittent cycle of 30 minutes. Then, the drain valve 17 is closed and the intermittent valve 18 is opened and the procedure continues as described above. Thus, a small amount of fluid is removed for every cycle.

Alternatively, such fluid removal may be performed only each fifth cycle or at any time desired.

The fluid removal does not need to be synchronized with the replenishment. If the patient feels or suspect or measures that the pressure inside the peritoneal cavity increases, for example so that the patient feels discomfort, the patient may operate a drain button, which drains a predetermined amount of fluid by opening the drain valve 17 and operating the flow pump 15 in the forward direction until a predetermined amount has been removed, for example 100 ml.

In another alternative embodiment, there is a pressure sensor, which activates a drain cycle if the pressure inside the peritoneal cavity increases above a predetermine threshold, see further below. The drain can also take place at predetermined time intervals, for example each hour.

It is noted that the amount of peritoneal fluid inside the peritoneal cavity should be optimal, so that the entire peritoneal membrane is used for exchange of ultrafiltration water, which promotes ultrafiltration, but so that as small as possible overpressure exists inside the peritoneal cavity, which counteracts ultrafiltration. If the installed volume is too small, only a portion of the peritoneal membrane is used, requiring higher glucose concentrations for achieving a desired ultrafiltration goal. If the pressure is too high, water is pressed back into the tissue and blood vessels.

The dosage of glucose may be determined in advance and adjusted according to a prescription by a doctor. The patient may also adjust the replenishment of glucose, at least within some limits. For example, if the patient feels pain, this may be due to a too high glucose concentration, and the patient may decrease such concentration by pressing a button. Pressing the button may result in reduction of glucose replenishment during the next few cycles. Other situations when a decreased replenishment of glucose should be contemplated may be if the patient feels dizziness or the blood pressure decreases.

According to an embodiment, glucose is added by a prescribed amount per hour, for example 5 gram glucose per hour. If the glucose concentration in bag 26 is 20% (200 gram per liter) and if a cycle is performed three times per hour, then 8.3 ml glucose fluid should be added each cycle to 100 ml peritoneal fluid exchanged each cycle. The concentration in the peritoneal fluid inside the peritoneal cavity will reach a concentration value, at which the consumption will be 5 gram glucose per hour. This will correspond to a desired ultrafiltration for one treatment period, which may be 10 hours during the day, or 6 to 8 hours during the night. The ultrafiltration is measured, and the prescription of the amount of glucose per hour is adjusted accordingly. The amount of glucose absorbed by a person is highly individual and may also change over time for a specific patient.

The embodiment described above is used when the patient has a single lumen patient line. However, the glucose concentration will vary slightly within the intermittent period, up and down around a mean value.

The intermittent period should be small compared to the variation of glucose in the peritoneal cavity. If no replenishment takes place, glucose is absorbed during a period of approximately one to three hours. Thus, the intermittent period for replenishment should be no longer than one hour. A suitable replenishment cycle or period may be 60, 50, 40, 30 or 20 minutes. The replenishment period is calculated as the time between the start of each replenishment cycle.

Figure 2:
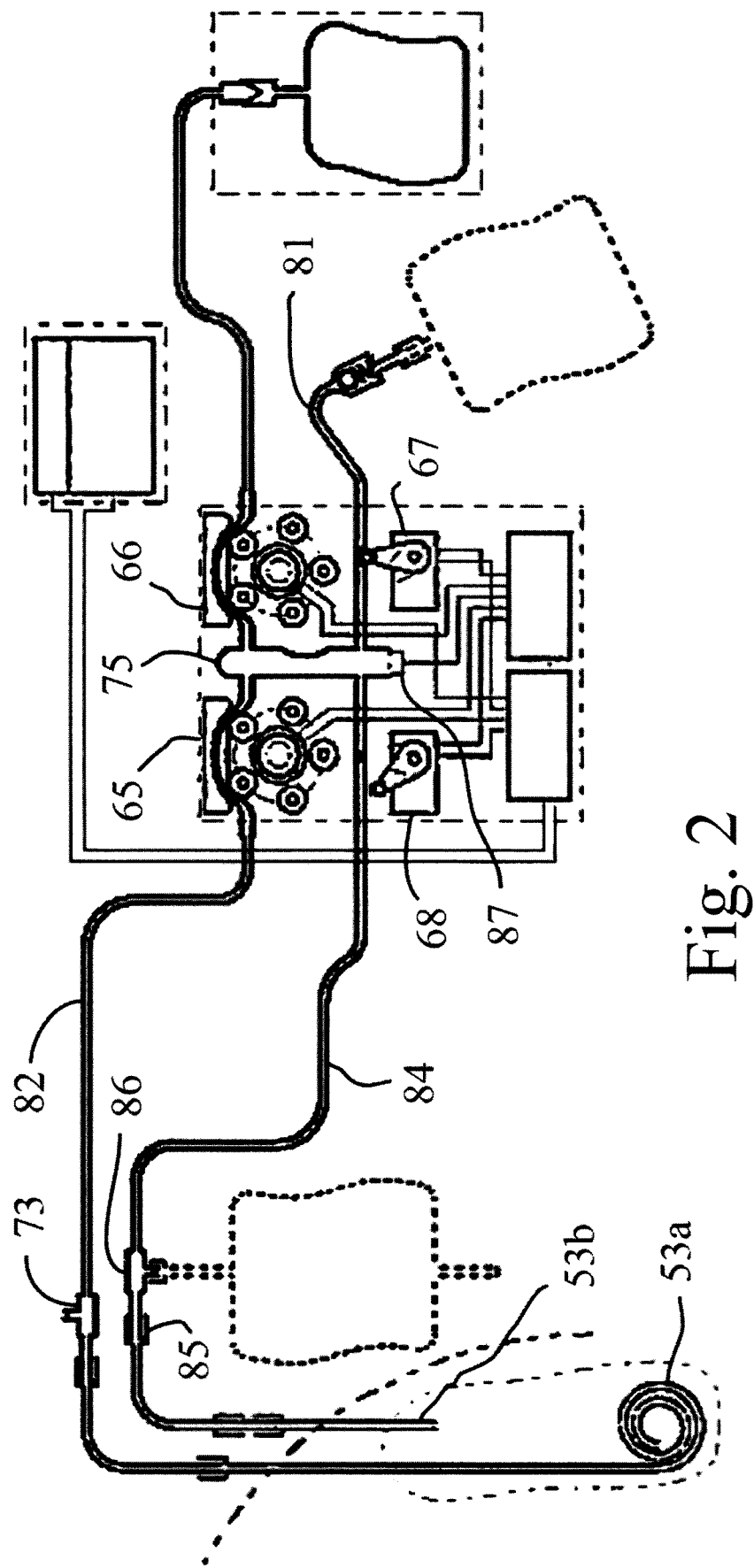
FIG. 2 is a schematic diagram of a second embodiment of the apparatus for providing an ultrafiltration fluid to a patient.

In another embodiment shown in FIG. 2, two patient line or catheters 53a and 53b are installed in the peritoneal cavity as shown. The two catheters may be arranged as a dual lumen catheter as is well-known.

In the second embodiment, the second catheter 53b is connected instead of or replacing the intermittent bag 33 in the embodiment of FIG. 1.

In the second embodiment, the flow pump 65 may continuously circulate peritoneal fluid into the peritoneal cavity via the second catheter 53b and out from the peritoneal cavity via the first catheter 53a, by operating the flow pump 65 in the forward (clockwise) direction and by opening the intermittent valve 68. The glucose pump 66 is also operated continuously for continuous replenishment of glucose. In this manner, a constant glucose concentration may be obtained in the peritoneal fluid introduced into the peritoneal cavity.

Alternatively, the glucose pump may be operated intermittently, with short intervals, for example one action per minute, or with longer intervals, such as each fourth minute.

The tube set according to the second embodiment comprises a patient line connector 85 instead of the intermittent bag 33 of the embodiment of FIG. 1. In addition, a sample port 86 is arranged adjacent the connector 85 in the intermittent tube 84.

In other respects, the operation is substantially the same as in the first embodiment described in connection with FIG. 1.

The concentrated glucose delivered by the glucose bag is mixed with the peritoneal fluid inside the cassette 75, wherein a thorough mixing will take place. Because the cassette has a predetermined inner volume of for example 5 ml, a sufficient time for mixing will prevail.

The patient having heart failure may also have low blood pressure, which may compromise the operation of the kidney. The kidney may require support in removal of excess water, since the urine production is smaller than normal. However, the excretion of metabolic waste products, such as urea and creatinine, may normally be sufficient.

However, because of the low urine volume, an insufficient removal of sodium may prevail. Thus, the peritoneal fluid used in these embodiments may be modified by reducing the sodium concentration in the initially installed peritoneal fluid to for example to 90 mmol/l, which results in removal of sodium, in addition to removal of water as described above. If the removal of potassium of the kidney is too low, a lowering of the potassium concentration to 1 mmol/l in the starting fluid may be appropriate, or even no potassium in the installed peritoneal fluid. However, the body is sensitive to low potassium concentration in blood, and a lowering of the potassium concentration (or zero) should be carefully supervised by a doctor.

The patient having heart failure may have a compromised blood pressure as indicated above. Such blood pressure may result in partial withdrawal of capillaries in the peritoneal membrane and adjacent tissue, resulting in less exchange of substances between the fluid in the peritoneal cavity and the blood. The result is less ultrafiltration. However, the continuous supply of glucose is expected to reduce any tendency for the capillaries to withdraw, since the body is not exposed to transient conditions. Thus, the continuous, or almost continuous but intermittent, replenishment of glucose is expected to be of great importance for sensitive patients.

The peritoneal membrane is sensitive to excessive exposure to glucose, which may result in peritoneal pain and peritonitis and other complications. A gentle exposure of the peritoneal membrane to glucose may counteract such problems. Accordingly, the initial installation of PD-fluid into the peritoneal cavity may take place with a low concentration of glucose, or even zero glucose. Then, the concentration of glucose is increased slowly during a predetermined time, such as 30 to 60 minutes, to the desired concentration.

Due to the fact that a replenishment of glucose is made continuously or intermittently with short intervals, a low concentration of glucose may be used and still a desired ultrafiltration may be achieved. This is advantageous for avoiding pain and peritonitis as well for maintaining the ultrafiltration function of the peritoneal membrane.

The replenishment of glucose may be controlled or monitored by measuring the glucose concentration in the effluent fluid from the peritoneal cavity. Suppose that the initial concentration of glucose is 1.5% and the measured concentration in the effluent fluid after 30 minutes has been reduced to 1.3%. In this case, a replenishment of glucose so that the inflowing fluid has a concentration of 1.7% may be appropriate. If the effluent fluid glucose concentration still decreases, the replenishment is increased further, to 1.8%, etc. On the other hand, if the effluent concentration is approaching the desired 1.5%, the replenishment is decreased.

If the patient during the treatment is exposed to hypotension or other problems, resulting in withdrawal of capillaries in the peritoneal membrane, this is manifested as a lowering of the ultrafiltration and a lowering of glucose absorption. The lowered glucose absorption may be monitored by a glucose sensor or meter and may result in an alarm to the patient and/or supervising persons. Then, the treatment may be interrupted or other actions undertaken for removing the cause of decreased absorption and low ultrafiltration.

On the other hand, excessive absorption of glucose to the blood may be encountered during certain conditions, resulting in low glucose concentration.

A glucose meter may be arranged in the sample ports 73, 86, 23. Alternatively, a glucose meter may be arranged in the tube set, for example adjacent the cassette 25, 75.

Figure 3:
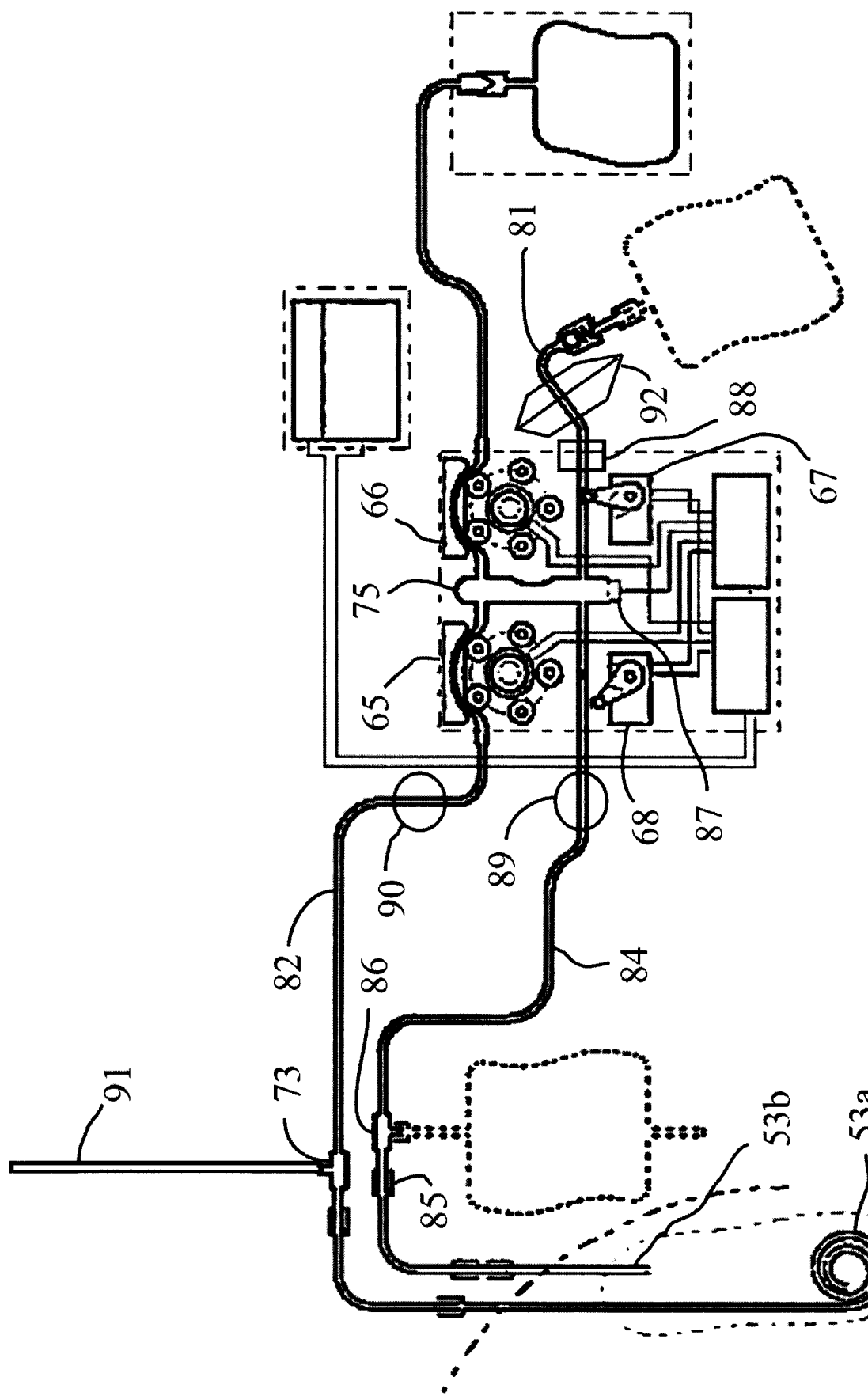
FIG. 3 is a schematic diagram of a third embodiment of the apparatus for providing an ultrafiltration fluid to a patient.

Since a glucose meter may be sensitive to constant exposure to glucose, the glucose meter 88 may be arranged in the drain tube 31, 81 after the drain valve 17, 67 as shown in FIG. 3. When the glucose concentration should be measured, the drain valve 67 is opened and the pump 65 is operated in a forward direction for a short time period and the measurement is performed. In this way, the glucose meter 88 is exposed for glucose only during short intervals.

A pressure sensor or meter 91 may be arranged in the ports 23, 73, 86 or any other position in the tube system in order to monitor or measure the pressure at or adjacent the connections to the patient line 3, 53a, 53b. A high pressure during standstill of the flow pump 65 may be indicative of too high a volume inside the peritoneal cavity. Thus, removal of some fluid to drain may be proper as indicated above.

The pressure meter 91 may be a tube of a suitable length connected to the port 73 as indicated in FIG. 3. Fluid will rise inside the tube and the height of the water pillar indicates the pressure, for example in cm waterpillar. Other arrangements may be used, such as a similar pressure meter in port 86 and/or port 23. In some embodiments, a pressure meter indicating a pressure below atmospheric pressure may be useful, since normally the pressures are always above or equal to atmospheric pressures. If a pressure below atmospheric pressure during a long time is measured, an alarm may be triggered.

A high pressure in port 23 during filling may depend on a partial occlusion of the patient line 3. A partial occlusion of the patient line would also result in a low pressure during emptying of the cavity. Thus, an alarm may be triggered.

If there is an occlusion or kink of the tube to the patient, i.e. the intermittent tube 84 in the second embodiment, this will be manifested as a high pressure in the cassette during operation of the flow pump 65. A pressure monitor or meter 87 arranged in the cassette may detect such a high unexpected or undesirable pressure and results in an alarm and/or other action of the apparatus, such as shut-down of the operation. The pressure monitor may be a piezo-electric pressure meter, which emits an electric signal substantially proportional to the pressure inside the cassette.

The pressure meter 37, 87 may also be used for controlling the operation of the flow pump and/or the glucose pump. By closing the intermittent valve 18 and the drain valve 17 and operating the flow pump 15 in the forward direction, a pressure should build up in the cassette 25, which may be controlled by the pressure meter 37, 87. The same control of the glucose pump may be performed. If pressure does not build up, a leak may exist.

The pressure of the pressure meter 37, 87 may be measured or monitored continuously. If a sudden and unexpected deviation of pressure is measured, an alarm is activated. This may happen if there is a kink on any of the tubes. If the valves do not operate properly, this may also be detected by the pressure monitor.

If there is a kink or occlusion at the patient line 82 during forward operation of the flow pump 65, a low-flow or no-flow will occur. This fact may remain undetected by the cassette pressure meter 87. However, a flow meter 90 arranged at the patient line 82 immediately before the pump segment may be used to detect a too small or absent flow. In addition, another flow meter 89 may be arranged between the intermittent valve 68 and the patient connector 85.

The treatment is continued during a long time, at least six hours. In an embodiment, the treatment is performed daily during 16 hours. In another embodiment, the treatment is nocturnal and last for 8 hours. Before the treatment, a new peritoneal fluid is introduced and after the treatment, all peritoneal fluid is drained. The difference between installed and removed fluid may be measured in order to calculate obtained ultrafiltration.

It is known that peritoneal dialysis may result in large losses of albumin—a loss of up to 10 grams per day has been reported. Patients having overload of water, such as congestive heart failure patients, are extra sensitive to loss of albumin. This is because during water exchange between blood and tissue, albumin plays a decisive role in such a water balance. In addition, such patients often are malnourished and have difficulties in replenishing the albumin in the blood. Thus, any removal of albumin should be counteracted.

FIG. 3 shows an albumin filter 92 arranged in the drain tube 81. The filter 92 will ensure that all substances equal to or larger than albumin will not pass to the drain bag 30. The final drain process starts with opening of drain valve 67 and closing intermittent valve 68 and operating pump 65 in the forward direction until all peritoneal fluid has been pumped out of the peritoneal cavity. All albumin will be retained by the albumin filter 92. After the peritoneal cavity has been emptied, the pump 65 may be operated in the reverse direction, in order to return a small amount of fluid to the peritoneal cavity. Such a small amount may be larger than the volume of tube 82 and cassette 75, such as about 20 ml. Such reverse flow will return all albumin accumulated inside the filter to the peritoneal cavity. The albumin is recovered by the lymph system of the body.

The same principle may be used in any of the other embodiments.

The albumin filter may be arranged anywhere in the drain tube 81, for example integrated in the connector 32 between the drain tube and the drain bag. In this manner, the filter may be exchangeable.

Another important fact assists in saving albumin, namely that no adsorption filter or dialyzer is arranged in the flow path during the replenishment cycles.

Adsorption filters may be used in conventional peritoneal dialysis for adsorption of waste products not cleared by the failing kidney, such as urea and creatinine. Such adsorption filters may adsorb albumin, which would risk to aggravate the symptoms for a congestive heart failure patient. The present embodiments do not use any filters comprising material that may adsorb albumin during the treatment time. To the contrary, the tube set is as small as possible and has no obstacles in the flow path, except for the pump 15 and the pinch valve 18. Finally, during the drain phase, the fluid passes through an albumin filter, which retains the albumin, which is then returned to the peritoneal cavity and may be absorbed by the body lymph system. Thus, albumin loss is minimized.

In addition, the flow path does not comprise a dialyzer having large surfaces, at which albumin may attach and be removed.

In addition, the tube set has a very small inner volume, about 10 ml plus the volume of the cassette, which may be about 5 ml.

It may be advantageous to agitate the peritoneal fluid in the peritoneal cavity. In the embodiment according to FIG. 2, such agitation may be performed by operating the flow pump 65 in the reverse direction during a predetermined time of for example 5 minutes followed by normal flow direction by operating the flow pump 65 in the forward direction. The operation in the reverse direction may be performed at a higher speed than normal or at varying speeds. In the first embodiment according to FIG. 1, an agitation may be obtained by operating the flow pump 15 with different speeds during the inflow of peritoneal fluid, for example 30 seconds of high speed followed by several minutes of normal speed. Operation with different speed may also or alternatively be used in the second embodiment.

The flow speeds during operation of the apparatus should normally be small in order not to exert unnecessary pressure on the peritoneal cavity and membrane. A flow speed of 15 ml/min to 40 ml/min is appropriate. The glucose pump may operate at speeds of 0.1 ml/min to 3 ml/min. During drain, the flow pump 65 may be operated at a higher speed of up to about 170 ml/min.

The glucose bag may comprise glucose at a concentration of 10% to 20% (up to 40%) and may have a volume of about 0.25 to 0.5 liter. The volume of peritoneal fluid entered into the peritoneal cavity may be about 1 to 3 liter, for example 1.5 liter. The peritoneal fluid may comprise ions of sodium 132 mM (mmole/liter), potassium 2 mM, calcium 2.5 mM, magnesium 0.5 mM, chloride 95 mM and lactate 40 mM. Lactate may be replaced by acetate or bicarbonate. The initial glucose concentration may be about 1.5% or lower, as indicated above.

The fact that glucose is added from a glucose concentration bag is advantageous, since glucose concentration can be sterilized without formation of toxic end products (AGE:s).

If sodium ions should be removed, the sodium ion concentration may be lowered to 95 mM or lower. The potassium concentration may be lowered to 1 mM or less (0 mM).

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. An apparatus for ultrafiltration of a patient, which patient has a peritoneal fluid in a peritoneal cavity, comprising:
   a cassette having first, second, third and fourth ports;
   a patient tube including a patient connector provided at one end of the patient tube and configured to be connected to a patient line for access to the peritoneal cavity of the patient, another end of said patient tube being configured for connection to said first port of the cassette, wherein the patient tube further includes a flow pump configured for removing and returning of a portion of said peritoneal fluid between the cassette and the peritoneal cavity using said patient tube;
   an intermittent bag and an intermittent tube for connection of the intermittent bag to said second port of the cassette, wherein the intermittent tube includes an intermittent valve, whereby said intermittent bag and intermittent tube are configured to receive said portion of said peritoneal fluid being removed from the peritoneal cavity through said patient tube by said flow pump and return said portion of said peritoneal fluid to the peritoneal cavity using said patient tube by said flow pump;
   a drain tube for connection of a drain bag to said third port of the cassette, wherein the drain tube includes a drain valve;
   a glucose tube for connection of a glucose bag configured to provide concentrated glucose to said fourth port of the cassette, wherein the glucose tube includes a glucose pump for addition of concentrated glucose to the cassette;
   whereby the apparatus is configured to replenish glucose to said portion of said peritoneal fluid being returned to the peritoneal cavity from the intermittent bag through said patient tube by said flow pump to maintain a concentration of glucose substantially constant in the peritoneal cavity; wherein
   the patient connector, the patient tube, the first port of the cassette, the cassette, the intermittent tube, the intermittent bag, the second port of the cassette, are all arranged without any adsorbent material or dialyzer.

2. The apparatus of claim 1 wherein the intermittent bag is smaller than 400 ml.

3. The apparatus according to claim 1, wherein the intermittent bag is smaller than 200 ml.

4. The apparatus according to claim 1, wherein the intermittent bag is 160 ml or smaller.

5. An apparatus for ultrafiltration of a patient, which patient has a peritoneal fluid in a peritoneal cavity, comprising:
   a cassette having first, second, third and fourth ports;
   a patient tube including a patient connector provided at one end of the patient tube and configured to be connected to a patient line for access to the peritoneal cavity of the patient, another end of said patient tube being configured for connection to said first port of the cassette, wherein the patient tube further includes a flow pump configured for removing and returning of a portion of said peritoneal fluid between the cassette and the peritoneal cavity using said patient tube;
   an intermittent bag and an intermittent tube for connection of the intermittent bag to said second port of the cassette, wherein the intermittent tube includes an intermittent valve, whereby said intermittent bag and intermittent tube are configured to receive said portion of said peritoneal fluid being removed from the peritoneal cavity through said patient tube by said flow pump and return said portion of said peritoneal fluid to the peritoneal cavity using said patient tube by said flow pump;

a drain tube for connection of a drain bag to said third port of the cassette, wherein the drain tube includes a drain valve;

a glucose tube for connection of a glucose bag configured to provide concentrated glucose to said fourth port of the cassette, wherein the glucose tube includes a glucose pump for addition of concentrated glucose to the cassette;

whereby the apparatus is configured to replenish glucose to said portion of said peritoneal fluid being returned to the peritoneal cavity from the intermittent bag through said patient tube by said flow pump to maintain a concentration of glucose substantially constant in the peritoneal cavity; wherein the drain tube, which is arranged outside of the peritoneal cavity, includes an albumin filter for preventing albumin from passing to the drain bag during draining of the peritoneal cavity.

6. The apparatus according to claim 5, wherein the intermittent bag is smaller than 200 ml.

7. The apparatus according to claim 5, wherein the intermittent bag is 160 ml or smaller.

8. A method for ultrafiltration of a patient, which patient has a peritoneal fluid in a peritoneal cavity, comprising:

removing a portion of said peritoneal fluid from the peritoneal cavity to an intermittent bag in a flow path without concentration thereof, wherein said flow path comprises a patient connector, a patient tube, a flow pump, a cassette, an open intermittent valve, and an intermittent tube;

subsequent to said removing, returning said portion of said peritoneal fluid to said peritoneal cavity from said intermittent bag through said flow path;

during said returning of said portion of said peritoneal fluid, simultaneously adding concentrated glucose to the cassette by means of a glucose pump from a glucose bag containing said concentrated glucose for dilution of said concentrated glucose in said portion of said peritoneal fluid in said cassette;

repeating said removing and returning of said portion of said peritoneal fluid and said adding of concentrated glucose intermittently with a period of not greater than 60 minutes;

wherein the removed portion of said peritoneal fluid and the returned portion of said peritoneal fluid pass through said patient connector, said patient tube, said flow pump, said cassette, said open intermittent valve, and said intermittent tube, which all are free from adsorbent materials.

9. The apparatus according to claim 8, wherein the intermittent bag is smaller than 200 ml.

10. The apparatus according to claim 8, wherein the intermittent bag is 160 ml or smaller.

11. A method for ultrafiltration of a patient, which patient has a peritoneal fluid in a peritoneal cavity, comprising:

removing a portion of said peritoneal fluid from the peritoneal cavity to an intermittent bag in a flow path without concentration thereof, wherein said flow path comprises a patient connector, a patient tube, a flow pump, a cassette, an open intermittent valve, and an intermittent tube;

subsequent to said removing, returning said portion of said peritoneal fluid to said peritoneal cavity from said intermittent bag through said flow path;

during said returning of said portion of said peritoneal fluid, simultaneously adding concentrated glucose to the cassette by means of a glucose pump from a glucose bag containing said concentrated glucose for dilution of said concentrated glucose in said portion of said peritoneal fluid in said cassette;

repeating said removing and returning of said portion of said peritoneal fluid and said adding of concentrated glucose intermittently with a period of not greater than 60 minutes;

wherein the removed portion of said peritoneal fluid and the returned portion of said peritoneal fluid pass through said patient connector, said patient tube, said flow pump, said cassette, said open intermittent valve, and said intermittent tube, which all are free from dialyzers.

12. The apparatus according to claim 11, wherein the intermittent bag is smaller than 200 ml.

13. The apparatus according to claim 11, wherein the intermittent bag is 160 ml or smaller.

14. A method for ultrafiltration of a patient, which patient has a peritoneal fluid in a peritoneal cavity, comprising:

removing a portion of said peritoneal fluid from the peritoneal cavity to an intermittent bag in a flow path comprising a patient connector, a patient tube, a flow pump, a cassette, an open intermittent valve, and an intermittent tube;

subsequent to said removing, returning said portion of said peritoneal fluid to said peritoneal cavity from said intermittent bag through said flow path, while adding concentrated glucose;

subsequent to said returning, draining the peritoneal cavity of all peritoneal fluid present in the peritoneal cavity, after finalized ultrafiltration, by removing all peritoneal fluid from the peritoneal cavity through a drain flow path, until the peritoneal cavity is empty, wherein the drain flow path comprises said patient connector, said patient tube, said flow pump, said cassette, an open drain valve, and a drain tube to a drain bag, wherein said drain tube includes an albumin filter, reversing the flow pump and returning a drain fluid volume of peritoneal fluid from the drain bag via the albumin filter and said drain flow path to the peritoneal cavity in order to return albumin gathered by the albumin filter to the peritoneal cavity, wherein said drain fluid volume is sufficiently large for returning albumin accumulated inside the filter to the peritoneal cavity.

15. The method according to claim 14, wherein said drain fluid volume is larger than a volume of said patient tube plus a volume of said cassette.

16. The method according to claim 14, wherein said drain fluid volume is 5 ml in excess of a volume of said patient tube plus a volume of said cassette.

17. The method according to claim 14, wherein said drain fluid volume is 20 ml.

18. The apparatus according to claim 14, wherein the intermittent bag is smaller than 200 ml.

19. The apparatus according to claim 14, wherein the intermittent bag is 160 ml or smaller.

20. An apparatus for ultrafiltration of a patient, comprising:

a cassette having first, second, third and fourth ports;

an intermittent tube and an intermittent bag connected to said intermittent tube, said intermittent tube being connected to said second port of the cassette, wherein the intermittent tube includes an intermittent valve;

a patient connector and a patient tube for connection of said patient connector to said first port of the cassette, wherein the patient connector is configured for connection to a patient line for access to a peritoneal cavity of the patient including a peritoneal fluid;

a flow pump arranged in said patient tube for removal of a portion of the peritoneal fluid from the peritoneal cavity to the intermittent bag when the intermittent valve is open, through a first flow path, the first flow path including said patient connector, said patient tube, said flow pump, said first port of the cassette, said cassette, said second port of the cassette, said intermittent tube, said intermittent valve, and for return of said portion of the peritoneal fluid in said intermittent bag to said peritoneal cavity when the intermittent valve is open, through a second flow path, the second flow path including said intermittent tube, said intermittent valve, said second port of the cassette, said cassette, said first port of the cassette, said flow pump, said patient tube and said patient connector;

a drain tube for connection of a drain bag to said third port of the cassette, wherein the drain tube includes a drain valve;

a glucose tube for connection of a glucose bag containing concentrated glucose to said fourth port of the cassette, wherein the glucose tube includes a glucose pump for metering of glucose to the cassette for dilution of the glucose in said portion of the peritoneal fluid being returned from the intermittent bag to the peritoneal cavity in said second flow path for keeping a concentration of glucose substantially constant in the peritoneal cavity;

wherein said first flow path and said second flow path are identical and are arranged without any adsorbent material or dialyzer.

21. The apparatus according to claim 20, wherein the drain tube includes an albumin filter for preventing albumin from passing to the drain bag during draining of the peritoneal cavity.

22. The apparatus according to claim 20, wherein the intermittent bag is smaller than 200 ml.

23. The apparatus according to claim 20, wherein the intermittent bag is 160 ml or smaller.

* * * * *